United States Patent [19]

Anderson

[11] Patent Number: 4,857,071
[45] Date of Patent: Aug. 15, 1989

[54] NOVEL HAIR DYE AND METHOD OF USE

[75] Inventor: James S. Anderson, Danbury, Conn.

[73] Assignee: Clairol, Inc., New York, N.Y.

[21] Appl. No.: 88,185

[22] Filed: Aug. 21, 1987

[51] Int. Cl.$^4$ .................. A61K 7/13; C07C 87/60; C07C 119/10
[52] U.S. Cl. .......................... 8/414; 8/405; 8/406; 8/429; 564/273; 564/441
[58] Field of Search ............ 8/409, 405, 406, 414, 8/423, 429; 564/273, 441

[56] References Cited

U.S. PATENT DOCUMENTS

| 3,861,868 | 1/1975 | Milbrada | 8/414 |
| 3,971,821 | 7/1976 | Baumann et al. | 564/273 |
| 4,690,685 | 9/1987 | Grollier et al. | 8/415 |

FOREIGN PATENT DOCUMENTS

| 2457100 | 1/1981 | France | 8/414 |

OTHER PUBLICATIONS

Johnson, J. C. "Nitroanilines and Nitroamino phenols"; *Hair Dyes* Noyes Data Corporation, N.J. 1973 pp. 113–125.
Corbett, & (author); Venkataraman K (ed) *The Chemistry of Synthetic Dyes* Chapter VII pp. 508–519, Academic Press N.Y. 1971.
Chemical Abstracts 79(7): 42450h (Manecke et al. 1973).
Chemical Abstracts 53: 14843d (Sawicki et al.)
Chemical Abstracts 54: 10878F (Micheel et al.) 1960.
Chemical Abstracts 68(4): 14050g (Day et al.)
Chemical Abstracts 109(9): 73437b (Raeymaekers et al.)

*Primary Examiner*—Paul Lieberman
*Assistant Examiner*—Linda D. Skaling
*Attorney, Agent, or Firm*—Sandra M. Person

[57] ABSTRACT

The invention encompasses the use of nitroaminobenzaldehydes and nitroaminobenzylimines as hair dyeing agents.

11 Claims, No Drawings

NOVEL HAIR DYE AND METHOD OF USE

This invention relates to nitroaminobenzaldehydes and nitroaminobenzylimines and their use as hair dyeing agents.

BACKGROUND OF THE INVENTION

While numerous chemical compounds have been suggested for use as hair dyeing ingredients, either alone or in combination, nowhere in the literature is there to be found any teaching of the efficacy of the use of nitroaminobenzaldehydes and nitroaminobenzylimines as hair dyeing agents.

SUMMARY OF THE INVENTION

The present invention encompasses the use of nitroaminobenzaldehydes and nitroaminobenzylimines generally as hair dyeing agents for the coloring of human hair.

This invention also pertains to the use of nitroaminobenzaldehydes and nitroaminobenzylimines in combination with other ingredients conventionally employed in hair dyeing compositions to effect the coloration of human hair.

DETAILED DESCRIPTION OF THE INVENTION

The art of hair dyeing is replete with examples of numerous known chemical compositions employed either alone or in combination with other such chemical compositions and or in combination with a variety of carriers, diluents, buffering agents and activators to formulate a highly commercial product or products which often find great utility and acceptance in the hair care industry as coloring or dyeing formulations.

To our knowledge, the use of the classes of chemical compounds known as nitroaminobenzaldehydes and nitroaminobenzylimines described in the present invention has never been taught by the art. Furthermore, to our knowledge, the efficacy of this class of compounds as hair dyeing agents has never been been recognized.

The class of nitroaminobenzaldehydes compounds (2) and nitroaminobenzylimines (3, 4) useful as hair dyeing agents generally can be synthesized from the starting material (1) according to the following scheme:

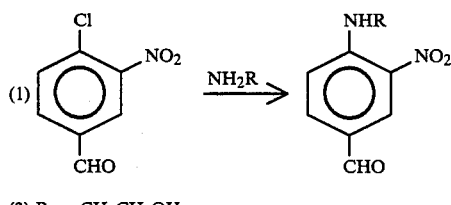

(2) R = CH₂CH₂OH

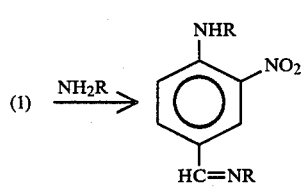

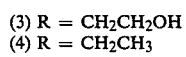

(3) R = CH₂CH₂OH
(4) R = CH₂CH₃

Generally, when treated with monoethanolamine (MEA) the starting material (1) yields a compound of formula (2) which is a nitroaminobenzaldehyde. Upon the use of more stringent reaction conditions, further reaction will occur to form the compound of formula (3) which is a nitroaminobenzylimine. When treated with ethylamine, the starting material yields the compound of the formula (4), which is nitroaminobenzylimine.

The synthesis of all of these compounds will be recognized as well within the ability of one skilled in the art and therefore requires no further elucidation. Typical methods of preparation for each are as follows:

Synthesis of 4-[(2-hydroxyethyl)amino]-3-nitrobenzaldehyde

Compound #2

With stirring, heat 3.71 g (0.02 moles) 4-chloronitrobenzaldehyde in a solution of 25 ml $H_2O$ + 25 ml monethanolamine to ca. 40° C. When TLC (silica support; 95:5 $CHCl_3$:MeOH eluent) shows no starting material, about 2 hrs., pour onto ice. Acidify to pH 5–6 with concentrated HCl and let stand overnight. Filter crystals and dry in vacuo at 50° C. Yield is 3.60 g (86%). $\lambda_{max}$ = 408 nm; log $\epsilon$ = 3.77 (95% ethanol)

Synthesis of N-(2-hydroxyethyl)-[4-(2-hydroxyethyl)amino]-3-nitrobenzylimine

Compound #3

With stirring, heat 15 g (0.08 moles) 4-chloro-3-nitrobenzaldehyde in 75 ml monoethanolamine to 60° C. When TLC (silica support; $CHCL_3$ eluent) shows no starting material, about 1.5 hrs., pour onto ice. Filter, wash (2×50 ml) with cold $H_2O$, dry in vacuo at 50° C. Yield is 20.5 g (100%). $\lambda_{max}$ = 407 nm; log $\epsilon$ = 3.73 (95% ethanol)

Synthesis of N-ethyl-(4-ethylamino-3-nitro)benzylimine

Compound #4

With stirring, reflux 5 g (0.027 moles) 4-chloro-3-nitrobenzaldehyde in 85 ml 70% ethylamine. Remove heat when TLC (silica support; toluene eluent) shows no starting material. Pour onto ice; then filter, wash (2×20 ml) with cold $H_2O$, dry in vacuo at 50° C. Yield is 5.6 g (94%). $\lambda_{max}$ = 405 nm; log $\epsilon$ = 3.67 (95% ethanol)

It has been found that all three compounds (2), (3), and (4) exhibit good dyeing characteristics when used for coloring human hair. Generally, all have good dye take on human hair, and yield good light properties and good wash-fastness properties.

Compound (2) exhibits a coloration which is yellow while compounds (3) and (4) show as more yellow-orange. All of the compounds of this class exhibit color properties which render them highly desirable as hair coloration formulation ingredients.

Table 1 shows the values obtained by a Hunter Tristimulus Colorimeter when blended gray hair and bleached hair are dyed with compounds 2–4 in a typical hair dye base.

TABLE 1

|  | Gray Hair | | | Bleached Hair | | |
| --- | --- | --- | --- | --- | --- | --- |
|  | L | a | b | L | a | b |
| Original hair | 33.83 | −1.04 | 7.58 | 61.57 | −0.70 | 17.41 |
| Compound 2 | 31.87 | −3.74 | 16.24 | 54.08 | −2.55 | 33.20 |
| Original Hair | 34.89 | −0.88 | 6.67 | 63.58 | −1.14 | 17.57 |
| Compound 3 | 33.80 | −3.92 | 14.08 | 58.03 | −5.60 | 29.50 |

TABLE 1-continued

|  | Gray Hair | | | Bleached Hair | | |
| --- | --- | --- | --- | --- | --- | --- |
|  | L | a | b | L | a | b |
| Original Hair | 33.16 | −0.90 | 7.50 | 61.71 | −0.67 | 17.41 |
| Compound 4 | 32.82 | −3.28 | 14.32 | 55.48 | −4.72 | 29.33 |

It is contemplated that not only the basic compounds, but also the group of compounds belonging to the class formed by adding various chemical substituents on the amino group will be of substantial utility as hair dyeing agents.

In particular, it is contemplated that the compounds of the class described herein above having alkyl, hydroxy- or poly-hydroxyalkyl and aromatic substituents will find the most utility, in addition to the base compounds described.

Specifically, we have found that the following compounds find utility as hair dyeing agents for the coloration of human hair.

| Compound Name | Structural Formula |
| --- | --- |
| 4-[(2-hydroxyethyl)amino]-3-nitrobenzaldehyde | 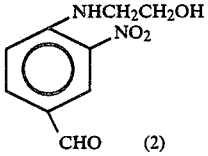 (2) |
| N—(2-hydroxyethyl)-4-[(2-hydroxyethyl)amino]-3-nitro benzylimine | 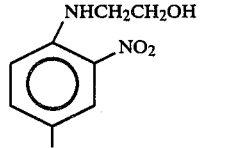 (3) |
| N—ethyl-(4-ethylamino-3-nitro)benzylimine | 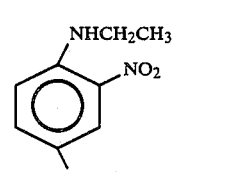 (4) |

| Compound Name | Structural Formula |
| --- | --- |

EXAMPLES

All of the components of the compositions utilized in exemplifying the present invention are commercially available ingredients, unless otherwise noted, and will be familiar to formulators of hair dyeing compositions. Consequently, the procedures for the preparation of such ingredients is not provided.

The following examples are set forth to illustrate the effectiveness of representative compounds of the present invention as hair dyeing agents.

Examples I–VI

A number of formulations having the compositions shown in the attached Table 2 were prepared and evaluated.

Each formulation was applied to laboratory hair swatches in a plastic weighing dish at ambient temperature and a pH of from 7–10. The application time varied from 15 to 30 minutes. At the end of this time the swatches of hair were shampooed lightly and rinsed. The light fastness and shampoo fastness of the compositions were determined using a Hunter Tristimulus Colorimeter before and after treatment. The yellow colors of the above dye formulations were found to be more lightfast and comparable in shampoo fastness to the yellow dyes currently used in other commercial products. The lightfastness of shades containing large amounts of these dyes as a proportion of the total dyes in the formula was very significantly better than any of known commercial dyes.

It has been found that hair dyeing formulations containing from about 2.0 wt% to about 0.001 wt% of one or more compounds of the present invention will be effective in achieving a highly desirable coloration of hair. Preferably from about 1.0 wt% to about 0.03 wt% of one or more of the compounds of this invention will be used in such hair dyeing formulations.

TABLE 2

| Composition Example # | Examples I–VI Amounts (Wt %) | | | | | |
| --- | --- | --- | --- | --- | --- | --- |
|  | I | II | III | IV | V | VI |
| Ethoxydiglycol | 4.00 | 4.00 |  |  | 1.80 |  |
| Ethanolamine | 1.50 | 2.00 |  | 0.50 |  |  |
| Diethanolamine |  |  | 3.00 |  | 2.00 | 2.00 |
| Cocamide DEA | 1.50 | 2.00 |  |  |  | 0.25 |
| Oleic Acid | 2.00 | 1.50 | 1.50 |  | 1.00 | 1.00 |
| Hydroxyethyl-cellulose | 1.10 | 1.00 |  |  | 0.80 | 1.20 |
| Isopropyl Alcohol |  |  | 1.00 | 5.00 |  | 0.05 |
| Propylene Glycol |  |  | 0.80 | 3.00 | 0.05 |  |
| Sodium Lauryl Sulfate | 0.20 |  |  | 3.00 | 0.05 |  |
| Nonoxynol-9 |  | 0.50 | 1.50 | 4.00 | 0.30 |  |
| Disperse Blue 1 |  | 0.030 |  |  | 0.250 | 0.050 |
| Disperse Blue 3 |  |  | 0.050 |  |  |  |
| Disperse Violet 1 |  | 0.050 |  |  |  | 0.090 |
| H.C. Orange No.1 |  |  |  |  | 0.018 | 0.020 |
| H.C. Red No. 1 |  |  |  |  | 0.006 | 0.005 |
| Disperse Black 9 |  | 0.060 | 0.050 |  | 0.140 | 0.140 |
| H.C. Red No. 2 |  | 0.150 | 0.150 |  | 0.016 | 0.020 |
| H.C. Blue No. 2 |  | 0.130 | 0.080 |  | 0.225 | 0.400 |
| Acid Orange 3 |  |  | 0.045 |  |  | 0.40 |
| Compound (2) | 0.500 |  |  |  | 0.220 |  |
| Compound (3) |  | 0.880 |  | 0.020 |  | 0.580 |

TABLE 2-continued

| Composition Example # | Examples I–VI Amounts (Wt %) | | | | | |
| --- | --- | --- | --- | --- | --- | --- |
| | I | II | III | IV | V | VI |
| Compound (4) | | | 0.200 | | | |
| Water | 89.200 | 87.700 | 91.625 | 84.480 | 92.175 | 94.105 |
| Total | 100.000 | 100.000 | 100.000 | 100.000 | 100.000 | 100.000 |
| Resultant shade of dyed swatch | Golden Blond | Reddish Brown | Ash Blond | Pale Blond | Light Ash Brown | Medium Ash Brown |

While the invention has been described with reference to a number of specific embodiments, it will be apparent to one skilled in the art that there are numerous additional variations which properly fall within the scope of this invention. Therefore, it should be understood that the foregoing embodiments and examples are set forth to illustrate the advantages to be achieved utilizing the present invention and should not be interpreted as limiting the scope of the invention specifically thereto.

What is claimed is:

1. A method of dyeing hair comprising applying to said hair an amount sufficient to dye same of at least one compound selected from the group consisting of: 4-[(2-hydroxyethyl)-amino]-3-nitrobenzaldehyde, N-(2-hydroxyethyl)-4-[(2-hydroxyethyl)amino]-3-nitro-benzylimine, and N-ethyl-(4-ethylamino-3-nitro)benzylimine.

2. The method according to claim 1, wherein said compound is 4-[(2-hydroxyethyl)amino]-3-nitrobenzaldehyde.

3. The method according to claim 1, wherein said compound is N-(2-hydroxyethyl)-4-[(2-hydroxyethyl)amino]-3-nitro-benzylimine.

4. The method according to claim 1, wherein said compound is N-ethyl-(4-ethylamino-3-nitro)benzylimine.

5. A hair dyeing composition containing
   (a) a hair dyeing effective amount of at least one compound selected from the group consisting of: 4-[2(hydroxyethyl)amino]-3-nitrobenzaldehyde, N-(2-hydroxyethyl)-4-[(2-hydroxyethyl)amino]-3-nitrobenzylimine, and N-ethyl-(4-ethylamino-3-nitro)-benzylimine;
   (b) a carrier, a surfactant; and
   (c) at least one ingredient selected from the group consisting of diluents, buffer agents and activators; wherein each of components (b) and (c) are present in cosmetically effective and acceptable amounts.

6. The composition according to claim 5, wherein said compound is 4-[(2-hydroxyethyl)amino]-3-nitrobenzaldehyde.

7. The composition according to claim 5, wherein said compound is N-(2-hydroxyethyl)-4-[(2-hydroxyethyl)amino]-3-nitrobenzylimine.

8. The composition according to claim 5, wherein said compound is N-ethyl-(4-ethylamino-3-nitro)benzylimine.

9. The composition according to claim 5, wherein said compound is present in an amount of from about 0.001 to about 2.0 wt%.

10. 4-[(2-hydroxyethyl)amino]-3-nitrobenzaldehyde.

11. N-(2-hydroxyethyl)-4-[(2-hydroxyethyl)amino]-3-nitrobenzylimine.

* * * * *